(12) United States Patent
Trofast et al.

(10) Patent No.: US 6,371,171 B1
(45) Date of Patent: *Apr. 16, 2002

(54) AGGLOMERATION OF FINELY DIVIDED POWDERS

(75) Inventors: Eva Ann-Christin Trofast; Magnus Olsson, both of Lund; Claes Ahlneck, Malmö , all of (SE)

(73) Assignee: Astra Aktiebolag, Sodertalje (SE)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/316,938

(22) Filed: Oct. 3, 1994

(30) Foreign Application Priority Data

Oct. 1, 1993 (SE) ................................ 9303215
Dec. 22, 1993 (SE) ................................ 9304270

(51) Int. Cl.[7] ............................................. A61K 31/00
(52) U.S. Cl. .......................................... 141/1; 428/402
(58) Field of Search ..................... 141/1, 2, 18, 21, 141/3, 20; 428/402

(56) References Cited

U.S. PATENT DOCUMENTS

| | | | | |
|---|---|---|---|---|
| 4,038,010 A | * | 7/1977 | Bremer | 425/314 |
| 4,039,480 A | * | 8/1977 | Watson et al. | 252/455 R |
| 4,129,419 A | * | 12/1978 | Hermann, Jr. | 422/64 |
| 4,161,516 A | | 7/1979 | Bell | 424/14 |
| 4,316,819 A | * | 2/1982 | Tu et al. | 252/430 |
| 4,495,308 A | * | 1/1985 | Gibson | 502/355 |
| 4,496,376 A | * | 1/1985 | Hradek | 96/112 |
| 4,514,300 A | * | 4/1985 | Szczesny et al. | 210/342 |
| 4,605,173 A | * | 8/1986 | Edmonds | 241/36 |

(List continued on next page.)

FOREIGN PATENT DOCUMENTS

| | | |
|---|---|---|
| DE | 41 05 984 A1 | 8/1992 |
| EP | 0 072 046 | 2/1983 |
| EP | 0 241 126 | 10/1987 |
| EP | 0 291 201 | 11/1988 |
| EP | 0 490 649 | 6/1992 |
| GB | 1242211 | 8/1971 |
| GB | 1520247 | 8/1975 |
| GB | 1569611 | 6/1980 |
| GB | 2 187 952 | 9/1987 |

OTHER PUBLICATIONS

Kugler, "Vibrating Screens for Aggregate Production", *Bulk Solids Handling*, vol. 6, No. 2, pp. 397–400 (Apr. 1986).
Pietsch, "Size Enlargement by Agglomeration", *John Wiley & Sons*, (1991).
Iinoya et al., "Powder Technology Handbook", (1991) Table of Contents Only.
Staffa et al., "Flowability of Powders under the Influence of Vibrations", *Powder Metallurgy International*, vol. 9, No. 1 (1977).
Pilpel, "Cohesive Pharmaceutical Powders", *Adv. Ph. Sc.*, vol. 3, pp. 173–219 (1971).
Neumann, "The Flow Properties of Powders", *Advaces in Pharm. Sci.*, vol. 2 (1967).
Claussen et al., "Kugelherstellung durch Pulveragglomeration", *J. of Materials Technology*, vol. 4, pp. 148–156 (1973).
Hicks et al., "Extrusion and Spheronizing Equipment", *Pharmaceutical Pellitization Technology*, pp. 86–98.

*Primary Examiner*—J. Casimer Jacyna
(74) *Attorney, Agent, or Firm*—Fish & Richardson P.C.

(57) ABSTRACT

A method of treating a finely divided powder is provided including a) forcing the powder through the apertures of a sieve to form agglomerates; and b) spheronizing the agglomerates. The method results in spheronized agglomerates having sufficient strength to withstand processing and packaging operations, but which are sufficiently soft to deagglomerate during delivery via a breath-actuated inhaler.

8 Claims, 4 Drawing Sheets

U.S. PATENT DOCUMENTS

Figure 1:
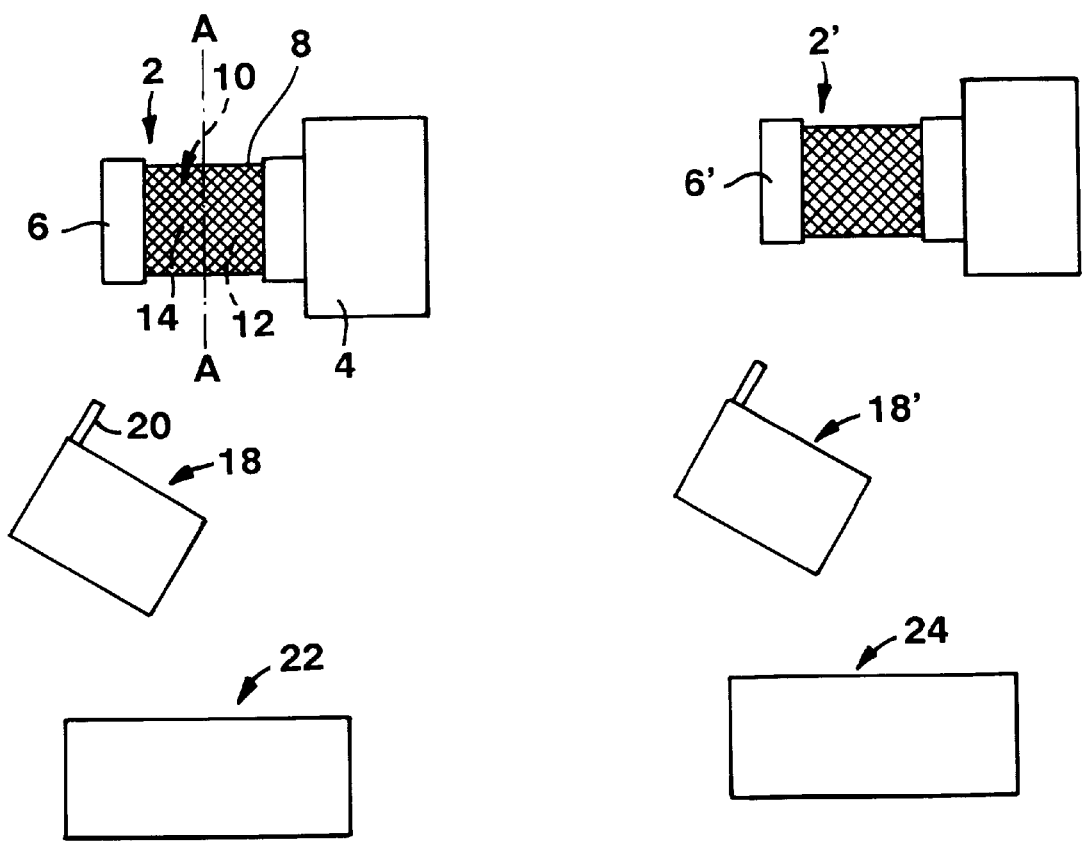
Figure 2:
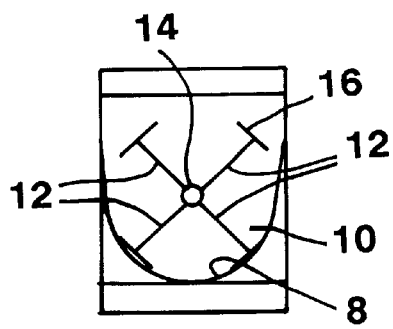
Figure 3:
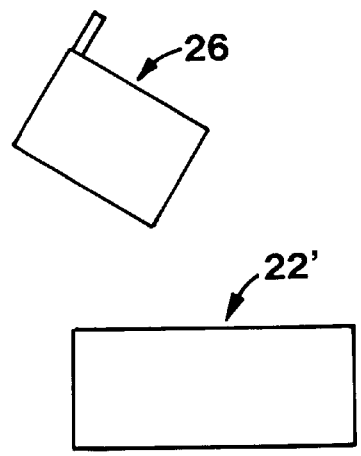

| | | | | |
|---|---|---|---|---|
| 4,655,701 A | * | 4/1987 | Moriya | 425/222 |
| 4,688,610 A | | 8/1987 | Campbell | 141/83 |
| 4,689,297 A | * | 8/1987 | Good et al. | 435/174 |
| 4,894,189 A | | 1/1990 | Dave et al. | 264/15 |
| 5,143,126 A | | 9/1992 | Boesch et al. | 141/1 |
| 5,262,172 A | * | 11/1993 | Sipos | 424/490 |
| 5,288,500 A | * | 2/1994 | Ibsen | 424/489 |
| 5,399,358 A | * | 3/1995 | Baichwal et al. | 424/464 |
| 5,547,567 A | * | 8/1996 | Madsen | 210/167 |

* cited by examiner

| NUCLEATION STEP | MSD MM | RSD % | MSV MM³ | RSD % |
|---|---|---|---|---|
| SIEVE 0.63 | 0.813 | 1.4 | 0.335 | 3 |
| SIEVE 1.0 | 0.851 | 7.4 | 0.433 | 9.8 |
| NO SIEVE | 3.18 | 13.3 | 73.2 | 92.1 |

AGGLOMERATION OF FINELY DIVIDED POWDERS

BACKGROUND OF THE INVENTION

The present invention relates to methods and devices for the agglomeration of finely divided powders, e.g., powdered medicaments for inhalation therapy.

Finely divided powders, i.e., powders having a very small particle size, typically less than 5–10 $\mu$m, are commonly used in inhalation therapy. In this application, the particle size of the powder is of the utmost importance. The diameter of the particles to be inhaled must be less than 10 $\mu$m or the particles will not adequately penetrate the bronchial area of the lungs. It is also very important in inhalation therapy that a precisely controlled dosage be administered. The inhaled route of administration enables the dose to be delivered directly to the airways, and thus allows a very small dosage to be given, minimizing side effects, but also making precise metering of the powder dosage crucial.

Particle size control and precise metering are often made problematic by the flow properties of finely divided powders. Most finely divided powders are light, dusty and fluffy. Further, the van der Waals forces of the particles exceed the force of gravity, causing the particles to be cohesive. This combination of properties make the powder flow poorly, complicating handling, processing and storage, and making it difficult to meter and dispense a precise dosage of the powder. The particles also tend to adhere to each other during storage and handling, forming agglomerates. Because these agglomerates are made up of a number of primary particles, they typically have diameters in excess of 10 $\mu$m. Accordingly, if the agglomerates do not break down into primary particles during inhalation the powder dosage will not properly penetrate the bronchial area. Also, if agglomeration is not controlled, random sized agglomerates may result, making precise metering of the powder difficult.

The flow properties of the powder can be improved by controlled agglomeration of the powder, e.g., by vibration, agitation or rolling of the powder with or without a binder. However, the agglomerates must have sufficiently low internal coherence so that they readily break into primary particles during inhalation in an inhalation device.

Methods of controlled agglomeration are known in the art. For example, Claussen and Petrow (Journal of Materials Technology, vol 4(3), pp. 148–156 (1973)) describe a method of agglomeration by tumbling in a cylinder tilted at an angle to the horizontal axis of rotation. U.S. Pat. No. 5,143,126 describes a vibratory conveyor for forming flowable agglomerates from previously poorly flowable fine-grained powder by subjecting the powder to a mechanical vibration step prior to transport and metering. GB 1,569,611 describes a process for agglomeration of a drug into soft pellets, using a binder to produce a paste which is extruded through a sieve to create agglomerates. GB 2,187,952 describes a method of agglomeration by kneading a crystalline powder as it is conveyed by conveying screws through an extruder.

SUMMARY OF THE INVENTION

The invention features a method of treating a finely divided powder that includes forcing the powder through a sieve to form agglomerates, and spheronizing the agglomerates. This process has been found to produce agglomerates having excellent handling properties, which have sufficient strength to withstand packaging and storage, but which are sufficiently soft so that they will easily break down into primary particles when they are expelled from an inhaler during inhalation therapy. In preferred embodiments, the agglomerates have a hardness of less than 100 mN, more preferably less than 20 mN, and most preferably between 0.5 and 20 mN as measured by a MHT-4 Microhardness tester (A. Paar, Austria).

The method is particularly suitable for use with finely divided powdered medicaments having a particle size of less than about 10 μm. In preferred aspects, the medicament is selected from the group consisting of terbutaline, budesonide and lactose. Typically, the agglomerates after the final step of the method have a diameter of less than about 2 mm, a bulk density of from about 0.2 to 0.4 g/ml, and a surface area of from about 2–20 $m^2/g$.

Preferably, the sieve comprises a U-shaped trough. In other embodiments, the sieve comprises a flat sieve having apertures greater than 0.5 mm, or a conical sieve.

In preferred aspects, the spheronization step comprises placing the agglomerates in a tilted container and rotating the container to tumble the agglomerates. Preferably, the container is a granulating pan, is provided with at least one scraper, and is tilted at an angle of from 10°–80° from the vertical. More preferably, the container is tilted at an angle of from 30°–60° from the vertical. Preferably, the spheronization step is performed for about 2 to 20 minutes and the container is rotated at a periphery speed of from about 0.5 to 1.0 m/s.

Preferably, the method further includes sizing the agglomerates by passing the agglomerates through a sieve. This sizing may take place after agglomeration, after spheronization, or both. Where the agglomerates are sized after spheronization, a subsequent spheronization step may be performed after this sizing step.

In another aspect, the method further includes metering a predetermined amount of the spheronized agglomerates into a breath actuated dry powder inhaler provided with means for deagglomerating the agglomerates during inhalation. In this aspect, the method may further include the step of actuating the inhaler, causing the agglomerates to be deagglomerated into primary particles by the means for deagglomerating. Other features and advantages of the invention will be apparent from the following description of a presently preferred embodiment and from the claims.

BRIEF DESCRIPTION OF THE DRAWINGS

FIG. 1 shows a schematic view of a device according to one embodiment of the invention.

FIG. 2 is a cross-sectional view of the device of FIG. 1 taken along line A—A.

FIG. 3 shows a schematic view of a modified device of FIG. 1.

FIG. 4 shows a schematic view of a device according to another embodiment of the invention.

FIG. 5 shows a schematic view of a modified device of FIG. 4.

FIG. 6 is a graph showing the particle size distributions resulting from each of the processing methods described in the Example.

FIG. 7 is a table showing the average sphere diameter (msd) and weight average sphere volume (msv), and relative standard deviation (rsd) for each measurement, for agglomerates obtained after eight minutes of spheronization in a stainless granulator as described in the Example.

FIGS. 8 and 8*a* show schematic views of a device according to yet another embodiment of the invention.

DESCRIPTION OF THE PREFERRED EMBODIMENTS

According to the invention the finely divided powdered medicament is supplied to a sieve and is forced through the apertures of the sieve by a mechanical device. During this treatment small, soft agglomerates or pellets are formed which are capable of breaking down to provide the finely divided medicament. These agglomerates can then be spheronized to obtain a more spherical, dense and stable form. The agglomerates resulting from the spheronizing process are harder than the agglomerates resulting from the agglomeration process, but are still capable of breaking down to provide a finely divided medicament which is able to penetrate the bronchial area.

Figure 4:
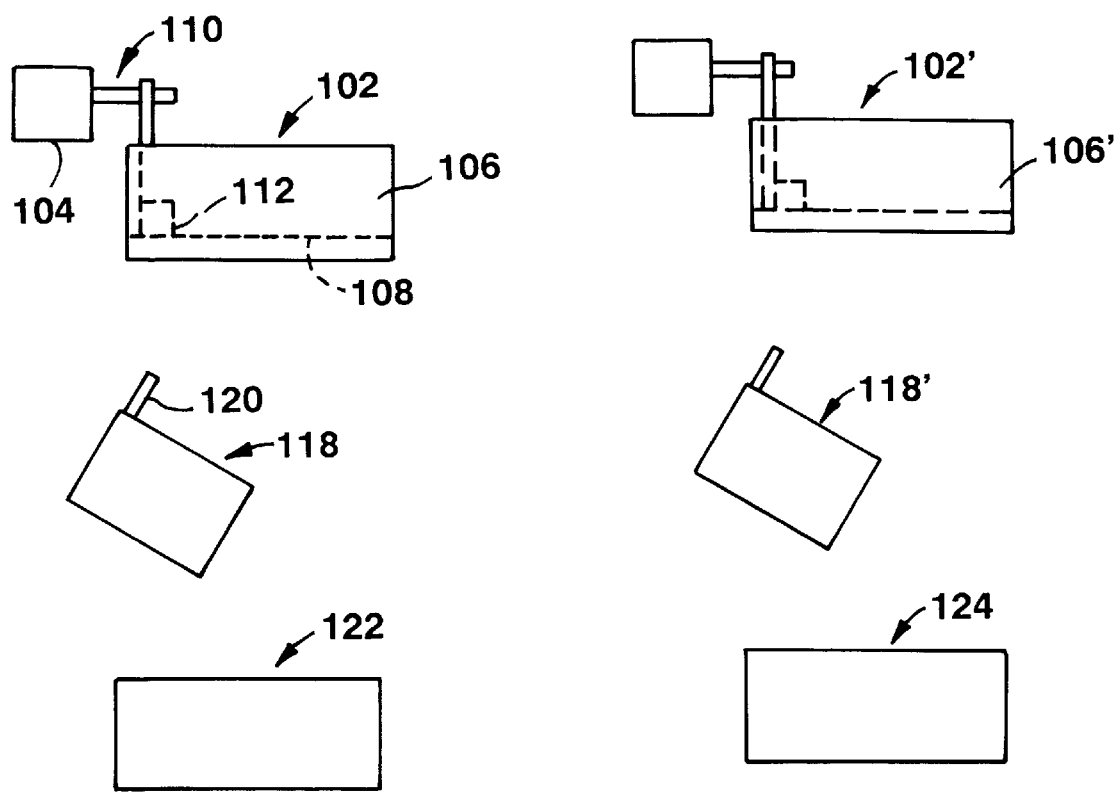

A device according to one embodiment of the invention is shown in FIG. 1. The sieve 2 which is used for agglomeration is formed in this embodiment as a substantially U-shaped trough 6. The walls of the U-shaped trough are made of a net 8 which may be of any rigid material, e.g., metal or rigid plastic.

The size of the resulting agglomerates will depend on the size of the apertures in net 8. To obtain agglomerates which have a size and form which make them suitable for the spheronization treatment which will follow, the size of the apertures is preferably between about 0.2 to 2.0 mm, more preferably between 0.3 to 1.0 mm.

Inside the U-shaped trough is disposed an oscillating and/or rotating device 10. Device 10 is preferably provided with at least one arm 12, mounted on a shaft 14 which is colinear with the longitudinal axis of the U-shaped trough 6 (see FIGS. 1 and 2). Preferably, device 10 is provided with four arms 12 mounted perpendicular to each other, as shown. At the end of each arm a plate 16 is mounted at a right angle to the arm 12 (FIG. 2). These plates will, due to the oscillating and/or rotating motion of device 10, force the finely divided powder supplied to the U-shaped trough 6 through the apertures in the net 8, thereby forming the agglomerates.

The shaft 14 of the oscillating device 10 is mounted in torque-transmitting engagement with a motor 4, or other driving means, which is provided to produce and transmit oscillating and/or rotational movement to the device.

Neither the feed rate of powder through the device nor the rate of oscillation and/or rotation is critical for proper agglomeration. Excessively high speeds may be undesirable, however, as they may lead to powder flying out of the trough.

As the agglomerates obtained from device 10 have different sizes and are comparatively soft, they need to be further treated to obtain the desired characteristics. The agglomerates are therefore collected in a spheronizing device, preferably a rotating pan or drum 18 which preferably is provided with one or more scrapers 20 (only shown schematically in the drawings), and which is tilted. Preferably the scraper is mounted so that it will contact and scrape down the inner wall of the pan as the pan is rotated, to prevent powder from sticking to the wall. The pan may be metal, plastic, or any other suitable material, so long as it is inert and does not contaminate the powder. It may be desirable to ground the pan to prevent build-up of electrostatic charges. A preferred type of pan is a "granulating pan", a type of granulating device that is well known in the art. The tilting angle of the pan or drum is preferably between 10°–80° from the vertical, more preferably between 30°–60°. The rotation of the tilted pan or drum 18 will make the agglomerates roll and tumble, causing the agglomerates to become "spheronized". The scraper increases rotation and tumbling of the agglomerates, and thus improves the spheronization.

This spheronization gives the agglomerates a stronger, more dense, compact and uniform form and a smoother outer surface. These improvements in form, hardness and density will further improve the flowability and the resistance of the agglomerates to breaking during handling and storage. The rotational velocity of the pan or drum determines the characteristics of the agglomerates after spheronization. Preferably, the periphery speed (the rotational velocity of the pan or drum measured at a point on its periphery) of the pan or drum is between 0.2–2.0, preferably between 0.5 –1.0 m/s. The spheronization time is preferably between about 2 to 20 minutes. After 20 min the agglomerates often have obtained the required optimal size, capability of breaking down to provide the finely divided medicament and density for their future use. The longer the agglomerates are spheronized, the harder and larger the agglomerates will become.

After the spheronization in the tilted pan or drum 18 the agglomerates are supplied to a sizing device, preferably a sieve 22 having an aperture size which is between 0.2–2.0 mm, preferably between 0.3–1.0 mm. This final sieving is used in order to obtain a uniform size of the agglomerates. This sieving step is typically necessary as a final processing step, to ensure uniformity. However, there may be some instances in which, due to the nature of the inhaler in which the agglomerates are to be used, sieving will not be necessary.

To minimize the number of agglomerates that are too large and therefore have to be discarded or undergo the entire agglomeration process again before they can be used, it is preferred to incorporate further steps of sieving and spheronization into the process. In a particularly preferred process, a further sieving step is incorporated into the process directly after the agglomeration process. After this sieving the agglomerates are spheronized in the granulating pan or drum and a second further sieving step is carried out after this spheronization. A second spheronization step is then carried out and the whole process is ended by the final sieving step. These further steps of sieving and spheronization will provide a more effective process and the agglomerates obtained after the second spheronization are uniform and have particularly desirable characteristics. An apparatus according to this embodiment of the invention is shown in FIG. 3.

As shown in FIG. 3, the finely divided powdered medicament is agglomerated in the substantially U-shaped trough 6' and the resulting agglomerates are supplied to the granulating pan or drum 18'. After the spheronization the agglomerates are supplied to a sieve 24 to obtain a more uniform size. After this sieving the agglomerates are spheronized a second time in a second granulating pan or drum 26.

This second granulating pan or drum 26 is of the same type as the first pan or drum 18' and the periphery speed and the spheronization time are as defined above for the first step of spheronization. After this second spheronization the agglomerates are sifted through the final sieve 22' to obtain a uniform size of the final product. The sifting is necessary as in some cases the agglomerates might grow too much during the spheronization and therefore the final product could contain agglomerates having a size larger than the required size. For example, this sifting is necessary when the particle size distribution exceeds from 0.2–2 mm. Preferably, final sifting is performed if the particle size distribution exceeds 0.3–1 mm.

In FIG. 4 a second embodiment of an apparatus for carrying out the method according to the invention is shown. In this embodiment the finely divided powdered medicament is supplied to a plain, substantially flat horizontal sieve 106 which is provided with a mechanical device 110 which forces the finely divided powder through the apertures of the net 108 in the sieve 106. During this extrusion of the powder through the apertures small, soft agglomerates or pellets will be formed which have the required characteristics for the following densifying treatment in the granulating pan or drum. Also in this embodiment the last step of the process includes a sieving of the agglomerates to obtain uniform size of the final product. The mechanical device which forces the powder through the apertures of the sieve could preferably be formed as a scraper 112 which describes a reciprocating movement over the net 108 of the sieve 106 and which during this movement forces the finely divided powdered medicament down through the apertures of the sieve 106. The size of the apertures of the sieve is related to the required size of the agglomerates. In this embodiment, the mesh size of the sieve is preferably greater than 0.5 mm. The preferred size of the apertures will give the agglomerates a size which makes them suitable for the following spheronization. Also in this embodiment of the invention the agglomerates resulting from the agglomeration process in the plain, substantially horizontal sieve 106 need to be further treated to obtain the desired characteristics. The agglomerates are therefore collected in 10 a rotating pan or drum 118 having one or more scrapers 120. The pan or drum is of the same type as described in relation to the first embodiment of the invention as well as the speed of the pan or drum and the spheronization time and angle. The process is thereafter finished by a final sifting in a sieve 122 as described in relation to the first embodiment.

Figure 5:
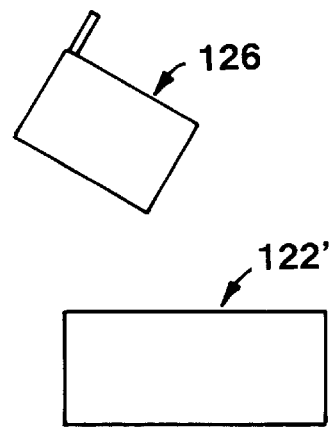

If required, the process according to this second embodiment can also be completed with the further steps of sieving and spheronization as described above in relation to the first embodiment of the method according to the invention. This alternative of the second embodiment is shown in FIG. 5, where a second sieve 124 and a second granulating pan or drum 126 is incorporated into the apparatus after the first granulating pan or drum 118' 30 and before the final sifting in the sieve 122'. The agglomeration process according to the invention will be illustrated by the following example.

EXAMPLE

Figures 6, 7:
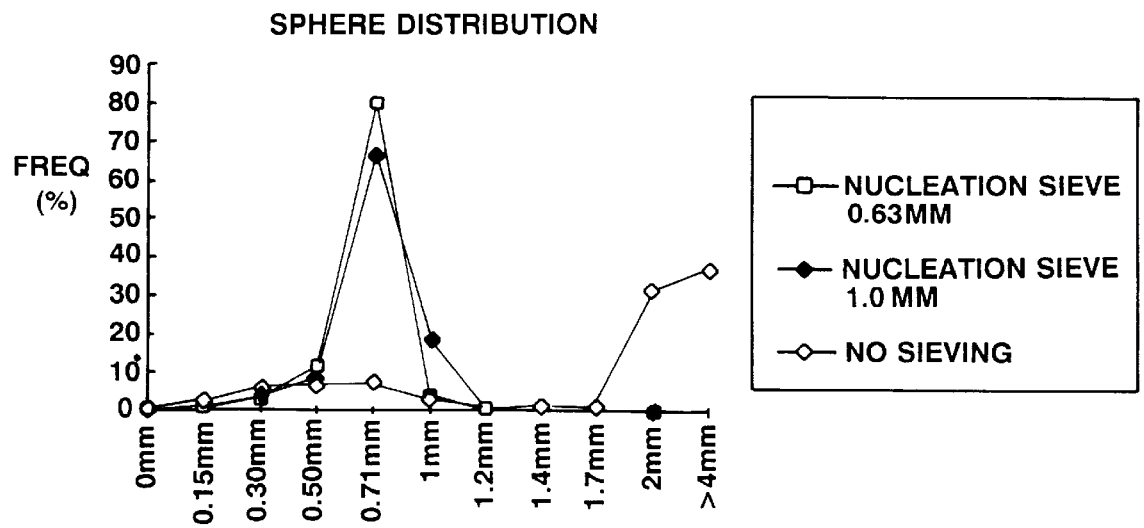

Micronized (mass medium diameter (MMD) 3.2 Wm and conditioned 25° C./50% RH) lactose was slowly added into an Erweka AR 400 oscillating device including a U-shaped sieve and four oscillating bars. By the action of the bars of the oscillating device the lactose was pushed through the sieve. The mesh size of the sieve net used was in one experiment 0.63 mm and in another experiment 1.0 mm. The oscillating frequency was in each case 90 turns/min. The agglomerates formed were collected and added to a stainless granulator (Eirisch type, 240 mm diameter), fixed at an angle of about 450 and equipped with a scraper. Tumbling of the agglomerates was performed at 50 rpm for 8 minutes. The resulting spheronized agglomerates were collected and analyzed for size distribution in a Retsch sieve with a mesh size up to 2 mm. For comparison, micronized and conditioned lactose was spheronized without prior treatment in the oscillating device. The relationship between the method of treatment (treatment in an oscillating device followed by spheronization vs. spheronization only) and the particle size distribution of the resulting agglomerates was studied. The results are shown in FIG. 6.

It is believed that agglomeration starts with particle-particle contact and adhesion (nucleation), forming small bodies which act as nuclei for further growth of the agglomerates. Since sieving through an oscillating device with a small sieve mesh produced nuclei of controlled size, fewer unagglomerated fine particles were left to increase the size of the agglomerates than in the powder which was spheronized without pre-treatment. The presence of many non-agglomerated fine particles during spheronization will lead to uncontrolled sphere growth and to larger variations in size distributions (as observed in FIG. 6) and a larger average sphere diameter and average sphere volume (as shown in FIG. 7). FIG. 7 shows the average sphere diameter (msd) and weight average sphere volume (msv), and the relative standard deviation (rsd) for each, for pre-treated and non-pre-treated spheronized agglomerates obtained after eight minutes of spheronization in a stainless granulator.

The above experiments clearly show the narrow distribution of the sphere sizes obtained in a U-shaped sieve as compared with a direct spheronization procedure of the primary finely divided powder. The experiments also illustrate that generally a small aperture mesh is preferred for processing in the oscillating device. Smaller apertures produce more uniform agglomerates, leading to a more uniform final product (see the results for 0.63 mm mesh vs. 1.2 mm mesh).

Other embodiments are within the claims. For example, the shape of the sieve can be varied, as could the size of the apertures.

Figure 8:
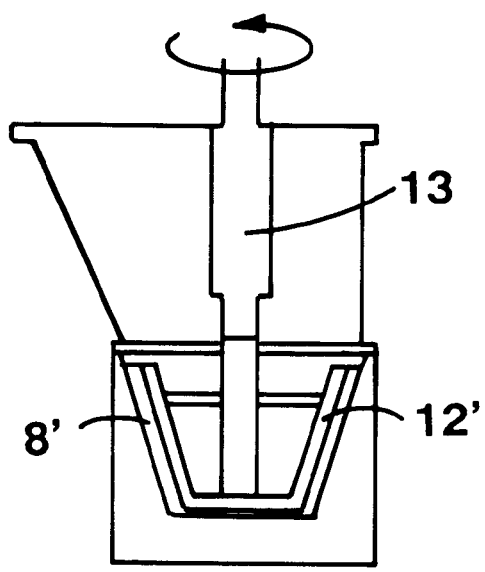
Figure 8A:
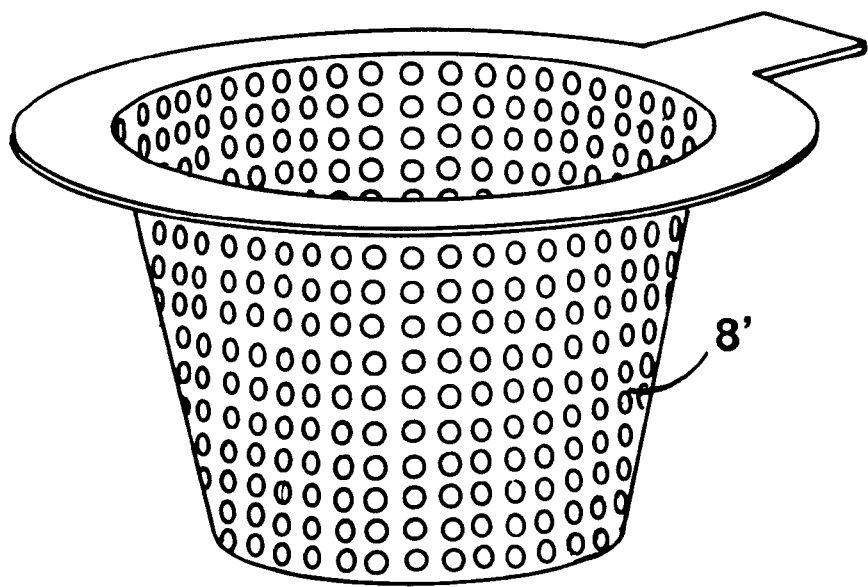

For example, sieve 8' can have a frustro-conical shape, as shown in FIGS. 8 and 8a, rather than being in the form of a U-shaped trough. In this case, the scraper preferably includes one or more members 12' which are mounted on a vertical shaft 13 and positioned such that rotation of the shaft causes the members to urge the powder through the apertures in the frustro-conical sieve.

The aperture size is selected based on the characteristics of the finely divided powdered medicament to be agglomerated. The suitable aperture size for a particular powder can be easily determined by those skilled in the art. The apertures of the sieve could also have any suitable shape, e.g. round, square, or any other desired shape.

It is also possible to modify the size, shape, speed and tilting angle of the granulating pan or drum thereby changing the size of the final agglomerates. The spheronization could also be done in a "Marumerizer", a commercially available apparatus for spheronization or granulation, or in any other suitable way using a rotatable rotation-symmetrical receptacle or container, e.g. any cylindrical or barrel-shaped container.

What is claimed is:

1. A method of treating a finely divided powder comprising the steps of:
    a) forcing the powder through the apertures of a conical sieve to form agglomerates; and
    b) spheronizing the agglomerates;
    further comprising the step of selecting the finely divided powder from the group consisting of terbutaline, budesonide and lactose.

2. A method of treating a finely divided powder comprising the steps of:
    a) forcing the powder through the apertures of a sieve having the form of a U-shaped trough to form agglomerates; and
    b) spheronizing the agglomerates.

3. A method of claim 2 further comprising selecting a sieve having apertures of a size between 0.2 and 2.0 mm.

4. A method of claim 3 wherein the sieve has apertures of a size between 0.3 and 1.0 mm.

5. The method of claim 2 wherein said sieve comprises an oscillating device having a plurality of oscillating bars positioned within the U-shaped trough, said method comprising the further step of:
oscillating the oscillating bars across a surface of the sieve having the form of a U-shaped trough in a manner to force powder through the sieve.

6. The method of claim 2 wherein the powder is substantially dry.

7. A method of treating a finely divided powder comprising the sequential steps of:
   a) forcing the powder through the apertures of an oscillating sieve having the form of a U-shaped trough, to form agglomerates;
   b) spheronizing the agglomerates;
   c) passing the agglomerates through a sizing sieve to produce a sample of agglomerates of substantially uniform size;
   d) repeating step (b); and
   e) repeating step (c).

8. A method of treating a finely divided powder comprising the sequential steps of:
   a) forcing the powder through the apertures of an oscillating sieve having the form of a U-shaped trough, to form agglomerates;
   b) spheronizing the agglomerates;
   c) passing the agglomerates through a sizing sieve to produce a sample of agglomerates of substantially uniform size;
   d) repeating step (b); and
   e) repeating step (c), wherein the powder is substantially dry throughout steps (a)–(e).

* * * * *